(12) United States Patent
Williams (10) Patent No.: US 9,506,082 B2
(45) Date of Patent: Nov. 29, 2016

(54) EUKARYOTIC EXPRESSION VECTORS RESISTANT TO TRANSGENE SILENCING

(75) Inventor: James A. Williams, Lincoln, NE (US)

(73) Assignee: Nature Technology Corporation, Lincoln, NE (US)

(*) Notice: Subject to any disclaimer, the term of this patent is extended or adjusted under 35 U.S.C. 154(b) by 255 days.

(21) Appl. No.: 13/082,666

(22) Filed: Apr. 8, 2011

(65) Prior Publication Data
US 2011/0250694 A1  Oct. 13, 2011

Related U.S. Application Data

(60) Provisional application No. 61/342,273, filed on Apr. 12, 2010.

(51) Int. Cl.
| C12N 15/00 | (2006.01) |
| C12N 15/09 | (2006.01) |
| C12N 15/11 | (2006.01) |
| C12N 15/63 | (2006.01) |
| C12N 15/85 | (2006.01) |
| C12N 15/86 | (2006.01) |

(52) U.S. Cl.
CPC ............... *C12N 15/85* (2013.01); *C12N 15/86* (2013.01); *C12N 2830/46* (2013.01)

(58) Field of Classification Search
None
See application file for complete search history.

(56) References Cited

U.S. PATENT DOCUMENTS

| 2006/0154370 A1* | 7/2006 | Chen ............................. 435/456 |
| 2009/0023671 A1* | 1/2009 | Brashears et al. ............... 514/44 |

FOREIGN PATENT DOCUMENTS

WO   WO 2008/153733   12/2008

OTHER PUBLICATIONS

Chen et al, Formation of a catalytically active dimer by tRNAval0driven short ribozymes, Nature Biotechnology, vol. 16, pp. 961-965 (1998).*
Kim et al, Improved Expression Vector Activity Using Insulators and Scaffold/Matrix-Attachment Regions, BioProcess International May 2006, pp. 24-31.*
Goetze et al, Performance of Genomic Bordering Elements at Predefined Genomic Loci. Molecular and Cellular Biology, Mar. 2005, p. 2260-2272.*
Van Bortle and Corces, tDNA insulators and the emerging role of TFIIIC in genome organization, Transcription 3:6, 1-8; Nov./Dec. 2012.*
Simms et al, TFIIIC Binding Sites Function as both Heterochromatin Barriers and Chromatin Insulators in *Saccharomyces cerevisiae*, Eukaryotic Cell, Dec. 2008, p. 2078-2086.*
Human HtV1 noncoding tRNA-like strands, GenBank: M15782.1, Apr. 1993.*
SIno Biological Inc, Human IL2 Gene cDNA clone plasmid, donwloaded Jun. 28, 2015.*
Recillas-Targa et al, Position-effect protection and enhancer blocking by the chicken_-globin insulator are separable activities, PNAS, 2002, vol. 99(10), pp. 6883-6888.*
Noma et al,A Role for TFIIIC Transcription Factor Complex in Genome Organization, Cell, 2006, Cell 125, 859-872.*
McFarlane and Whitehall, tRNA genes in eukaryotic genome organization and reorganization, Cell Cycle 8:19, 3102-3106; Oct. 1, 2009.*
Marck and Grosjean, tRNomics: Analysis of tRNA genes from 50 genomes of Eukarya, Archaea, and Bacteria reveals anticodon-sparing strategies and domain-specific features, RNA 2002 (8), pp. 1189-1232.*
Chancham et al., "Nucleic acid-matrix attachment recognition regions—as facilitators in plasmid transfer," *Journal of Drug Targeting*, May 2003, vol. 11(4), pp. 205-213.
Chenna et al., "Multiple sequence alignment with the Clustal series of programs," *Nucleic Acids Research*, 2003, vol. 31, No. 13, pp. 3497-3500.
Chen et al., "Improved Production and Purification of Minicircle DNA Vector Free of Plasmid Bacterial Sequences and Capable of Persistent Transgene Expression In Vivo," *Human Gene Therapy*, Jan. 2005, 16: 126-131.
Chen et al., "Silencing of episomal transgene expression by plasmid bacterial DNA elements in vivo," *Gene Therapy*, 2004, 11: 856-864.
Davie, "Inhibition of Histone Deacetylase Activity by Butyrate," *Journal of Nutrition*, 2003, 133:2485S-2493S.
Donze et al., "RNA polymerase III and RNA polymerase II promoter complexes are heterochromatin barriers in *Saccharomyces cerevisiae*," *The EMBO Journal*, 2001, vol. 20, No. 3, pp. 520-531.
Ehrhardt et al., "Optimization of Cis-Acting Elements for Gene Expression From Nonviral Vectors In Vivo," *Human Gene Therapy*, Feb. 2003, 14: 215-225.
Garrison et al., "Postintegrative Gene Silencing Within the Sleeping Beauty Transposition System," *Molecular and Cellular Biology*, Dec. 2007, vol. 27, No. 24, pp. 8824-8833.
Girod et al., "Use of the Chicken Lysozyme 5' Matrix Attachment Region to Generate High Producer CHO Cell Lines," *Biotechnology Bioengineering*, Jul. 2005, vol. 91, No. 1, pp. 1-10.
Irmer et al., "tRNA gene sequences are required for transcriptional silencing in *Entamoeba histolytica*," *Eukaryotic Cell*, Feb. 2010, vol. 9, No. 2, pp. 306-314.
Katz et al., "High-Frequency Epigenetic Repression and Silencing of Retroviruses Can be Antagonized by Histone Deacetylase Inhibitors and Transcriptional Activators, But Uniform Reactivation in Cell Clones is Restricted by Additional Mechanisms," *Journal of Virology*, Mar. 2007, vol. 81, No. 6, pp. 2592-2604.

(Continued)

*Primary Examiner* — Maria Marvich
(74) *Attorney, Agent, or Firm* — Medlen & Carroll, LLP (57) ABSTRACT

The present invention relates to recombinant DNA molecules such as plasmids, non-viral vectors, viral vectors and hybrids thereof, and more particularly to vector modifications that improve expression of said DNA molecules in cell lines and organisms.

7 Claims, 7 Drawing Sheets

(56) References Cited

OTHER PUBLICATIONS

Luke et al., "Improved antibiotic-free DNA vaccine vectors utilizing a novel RNA based plasmid selection system," *Vaccine*, 2009, 27: 6454-6459.

Lunyak et al., "Developmentally regulated activation of a SINE B2 repeat as a domain boundary in organogenesis," *Science*, Jul. 2007, vol. 317: 248-251.

Miao et al., "Long-term and therapeutic-level hepatic gene expression of human factor IX after naked plasmid transfer in vivo," *Molecular Therapy*, Jun. 2001, vol. 3, No. 6, pp. 947-957.

Nielsen et al., "Incorporating double copies of a chromatin insulator into lentiviral vectors results in less viral integrants," *BioMed Central Biotechology*, 2009, 9:13.

Simms et al., "TFIIIC binding sites function as both heterochromatin barriers and chromatin insulators in *Saccharomyces cerevisiae*," *Eukaryotic Cell*, Dec. 2008, vol. 7, No. 12, pp. 2078-2086.

Suzuki et al., "Plasmid DNA sequences present in conventional herpes simplex virus amplicon vectors cause rapid transgene silencing by forming inactive chromatin," *Journal of Virology*, Apr. 2006, vol. 80, No. 7, pp. 3293-3300.

Wang et al., "Silencing near tRNA genes requires nucleolar localization," *Journal Biological Chemistry*, Mar. 2005, vol. 280, No. 10, pp. 8637-8639.

West et al., "Insulators: many functions, many mechanisms," *Genes & Development*, 2002, 16: 271-288.

Williams et al., "Generic plasmid DNA production platform incorporating low metabolic burden seed-stock and fed-batch fermentation processes," *Biotechnology Bioengineering*, Aug. 2009, vol. 103, No. 6, pp. 1129-1143.

\* cited by examiner

EUKARYOTIC EXPRESSION VECTORS RESISTANT TO TRANSGENE SILENCING

CROSS REFERENCE TO RELATED APPLICATIONS

This application claims priority to U.S. Provisional Patent Application Ser. No. 61/342,273 entitled "Eukaryotic expression vectors resistant to transgene silencing" which was filed Apr. 12, 2010 the entire contents of which are incorporated herein by reference.

STATEMENT REGARDING FEDERALLY SPONSORED RESEARCH OR DEVELOPMENT

This invention was supported in part with government support under Grant No. 1R43GM080768-01, awarded by the National Institutes of Health. The government has certain rights in this invention.

FIELD OF THE INVENTION

The present invention relates to a family of eukaryotic expression vectors useful for gene therapy, genetic immunization, recombinant protein production and more particularly, to vector modifications that improve the expression of vector-encoded transgenes. Such recombinant DNA molecules are useful in biotechnology, transgenic organisms, cell culture production of recombinant proteins, gene therapy, therapeutic vaccination, and DNA vaccines.

BACKGROUND OF THE INVENTION

Eukaryotic expression vectors are utilized for various biomedical applications including protein production (in eukaryotic cell lines) from transient or integrated cell lines, and in vivo gene therapy, transgenic or vaccination applications.

A key barrier in this technology is that expression vectors maintained transiently, or stably integrated, undergo promoter inactivation (silencing) over time.

Transgene silencing of non-integrating vectors such as plasmid, AAV, adenoviral vectors, etc may be mediated by the prokaryotic region of the vector which has been linked to transgene silencing of plasmid vectors in transfected cell lines and in tissues in vivo (Chen Z Y, He C Y, Meuse L, Kay M A. 2004. *Gene Therapy* 11: 856-864).

Gene silencing is also a critical problem with stably integrated nonviral vectors (e.g. Sleeping beauty transposon; Garrison B S, Yant S R, Mikkelsen J G, Kay M A. 2007. Molecular Cellular Biology 27: 8824-8833) and viral vectors such as retroviral (Katz R A, Jack-Scott E, Narezkina A, Palagin I, Boimel P, Kulkosky J, Nicolas E, Greger J G, Skalka A M. 2007. J. Virol. 81: 2592-2604) and lentiviral (Nielsen T T, Jakobsson J, Rosenqvist N, Lundberg C. 2009. BMC Biotech. 9:13) vectors that also undergo promoter inactivation (silencing) over time. Silencing with these vectors is mediated by genomic DNA flanking the insertion site since the prokaryotic region of the vector is not integrated into the genome.

This lack of sustained transgene expression negatively impacts the cost of cell culture production of recombinant proteins, and has also limited the in vivo application of non-viral and viral vector systems to short term applications.

Various technologies have been developed to attempt to address this limitation.

Insulator elements: One strategy to reduce transgene silencing is to include boundary or insulator elements (e.g. scaffold or matrix attachment regions; reviewed in West A G, Gaszner M, Felsenfeld G. 2002. *Genes Dev* 16: 271-288) in the vector to insulate the transgene from integration site dependent inactivation. Multiple vector systems incorporating matrix attachment regions (MARs) have been developed and demonstrated to have utility. For example, incorporation of the Chicken Lysozyme 5' matrix attachment region into a plasmid has been shown to improve transgene expression in vitro with integrated and transient Chinese hamster ovary (CHO) cell culture systems (Girod P A, Zahn-Zabal M, Mermod N. 2005. *Biotechnol. Bioeng.* 91: 1-10) and in vivo from plasmid based non-viral vectors (Ehrhardt A, Peng P D, Xu H, Meuse L, Kay M A. 2003 *Hum Gen. Ther* 14: 215-225).

Minicircle vectors: An alternative strategy to prevent transgene inactivation is to remove the prokaryotic region of the plasmid. For example, minicircle and linear 'Minimalistic immunogenic defined gene expression' (Midge) vectors have been developed which do not contain a prokaryotic region. Removal of the prokaryotic region in minicircles improved transgene expression in transfected cell lines (Suzuki M, Kasai K, Saeki Y. 2006. *J. Virol.* 80: 3293-3300) and in animals (Chen et al., Supra. 2004).

Transgene silencing mechanisms: Non replicating transiently transfected plasmids are not inactivated by de novo methylation; this is not surprising, since methylation typically requires replication. Rather, the bacterial sequences within the vector appear to become associated with an inactive form of chromatin which then triggers transcriptional silencing of the entire vector (Suzuki et al., Supra, 2006). One strategy to reduce this effect is to clone a locus control region into the vector as described above. This partially alleviates silencing by blocking transcriptional inactivation (Miao C H, Thompson A R, Loeb K, Ye X. 2001. *Mol. Ther.* 3: 947-957). This data would indicate that the improvement observed with MARs and minicircle vectors are due to a similar mechanism: prevention of prokaryotic region mediated silencing by blockage (MARs) or removal (minicircles).

Current barriers: Methods to manufacture midge and minicircle vectors are expensive and not easily scalable. For example, optimal manufacture of minicircle DNA vectors yields only 2 mg of minicircle per liter culture (Chen Z Y, He C Y, Kay M A. 2005. *Hum Gene Therapy* 16: 126-131) compared to 2200 mg/L with optimized plasmid vectors and an inducible fermentation process (Williams, J. A., Luke, J., Langtry S., Anderson, S., Hodgson, C. P., and Carnes, A. E. (2009). *Biotechnol Bioeng* 103:1129-1143).

Matrix attachment regions are large (the commonly utilized chicken lysozyme 5' MAR is 3 kb; Girod et al., Supra, 2005); inclusion of this region therefore dramatically reduces the potency of a plasmid. As well, MARs are not a general solution since they improve expression only in certain cell lines (Chancham P, van Ljperen T, McDoom I, Hughes J A. 2003. *J Drug Targeting* 11: 205-213). Incorporation of large MAR sequences into limited payload integration vectors such as retroviral, lentiviral and transposon vectors is not feasible, and some complex chromatin insulators such as the chicken β globin insulator block lentiviral transduction (Nielsen et al., Supra, 2009).

There is clearly a significant need for more efficient methods to prevent prokaryotic region mediated transgene silencing of eukaryotic expression plasmids.

SUMMARY OF THE INVENTION

The present invention relates generally to methods of increasing the duration of transgene expression from vectors.

The present invention also relates generally to methods of increasing the duration of transgene expression from covalently closed supercoiled plasmid DNA vectors.

One object of the invention is to provide improved transgene expression duration plasmid vectors. Yet another object of the invention is to provide methods for improving transgene expression duration.

According to one object of the invention, a method of increasing transgene expression duration from covalently closed supercoiled plasmid DNA comprises modifying the plasmid DNA to add one or more components selected from the group consisting of: an RNA Pol III Type II promoter, tRNA promoter, SEQ ID NO: 2, RNA Pol III Type II promoter B-box, RNA Pol III Type II promoter A-box; and transferring the modified plasmid DNA into a vertebrate cell or organism.

According to another object of the invention, said methods of plasmid modification improve plasmid-directed transgene expression duration in subsequent cell culture and or transfected tissue.

According to one object of the invention, a method of increasing transgene expression duration from non-integrating vector DNA comprises modifying the vector DNA to add one or more components selected from the group consisting of: an RNA Pol III Type II promoter, tRNA promoter, SEQ ID NO: 2, RNA Pol III Type II promoter B-box, RNA Pol III Type II promoter A-box; and transferring the modified viral vector DNA into a vertebrate cell or organism.

According to another object of the invention, said methods of vector DNA modification improve vector-directed transgene expression duration in subsequent cell culture and or transfected tissue.

According to one object of the invention, a method of increasing transgene expression duration from genomically integrated vector DNA comprises modifying the vector DNA to add one or more components selected from the group consisting of: an RNA Pol III Type II promoter, tRNA promoter, SEQ ID NO: 2, RNA Pol III Type II promoter B-box, RNA Pol III Type II promoter A-box; and integrating the modified vector DNA into a vertebrate cell or organism.

According to another object of the invention, said methods of vector modification improve integrated vector-directed transgene expression duration in subsequent cell culture and or transfected tissue.

It is another object of the present invention to provide compositions of matter for construction of vectors.

According to one object of the invention, a composition for construction of a vector comprises one or more anti-silencing elements with at least 90% sequence identity to the sequence set forth as SEQ ID NO: 2, and a vector DNA replicon, wherein said anti-silencing element is operably linked to said vector DNA replicon. According to another object of the invention, said anti-silencing elements improve vector-directed transgene expression duration in subsequent cell culture and or transfected tissue.

Further objects and advantages of the invention will become apparent from a consideration of the drawings and ensuing description.

DEFINITION OF TERMS

AAV: Adeno-associated virus
A-box: Intragenic RNA Pol III promoter element present in Type II promoters (e.g. tRNA promoters)
AF: Antibiotic-free
ASE: Anti-silencing element
bp: basepairs
B-box: Intragenic RNA Pol III promoter element present in Type II promoters (e.g. tRNA promoters)
ccc: Covalently Closed Circular
CHO: Chinese Hamster Ovary mammalian cell line
CMV: Cytomegalovirus
DNA replicon: A genetic element that can replicate under its own control; examples include plasmids, cosmids, bacterial artificial chromosomes (BACs), bacteriophages, viral vectors and hybrids thereof.
*E. coli*: *Escherichia coli*, a gram negative bacteria
EGFP: Enhanced green fluorescent protein
gDNA: genomic DNA
GFP: Green fluorescent protein
Integrating vector: A vector that expresses one or more transgenes after integration into the target cell genome. For example, retroviral, lentiviral, transposon, phage phiC31 integrase vectors etc.
Kan: Kanamycin
KanR: Kanamycin Resistance gene
Kozak sequence: Optimized sequence of consensus DNA sequence gccRccATG (R=G or A) immediately upstream of an ATG start codon that ensures efficient tranlation initiation. A SalI site (GTCGAC) immediately upstream of the ATG start codon (GTCGACATG) is an effective Kozak sequence
MAR: Matrix attachment region
Neo: Neomycin
NeoR: Neomycin resistance gene
Non-integrating vector: A vector that expresses one or more transgenes without integration into the target cell genome. For example, plasmid, adenoviral, adeno-associated virus alphavirus, poxvirus, herpesvirus, SV40 virus vectors, etc.
PCR: Polymerase Chain Reaction
Plasmid: An extra chromosomal DNA molecule separate from the chromosomal DNA which is capable of replicating independently from the chromosomal DNA.
pUC origin: pBR322-derived origin, with G to A transition that increases copy number at elevated temperature
qRT-PCR: quantitative real time polymerase chain reaction
RNA Pol III: RNA polymerase III
shRNA: short hairpin RNA
TFIIIC: Transcription Factor for polymerase III C. TFIIIC binds the A and B box of RNA Pol III Type II promoters
tRNA: Transfer RNA, a short RNA transcribed by RNA Pol III Type II promoter: A class of RNA Pol III promoters including tRNA promoters that contains two intragenic promoter elements called the A box and B box.

Vector: A gene delivery vehicle, including viral (e.g. alphavirus, poxvirus, lentivirus, retrovirus, adenovirus, adenovirus related virus, SV40 virus, herpes virus etc) and nonviral (e.g. plasmid, midge, transcriptionally active PCR fragment, minicircles, bacteriophage, etc) vectors. These are well known in the art and are included herein by reference.

Vertebrate expression vector: A viral or nonviral gene delivery vehicle that expresses a transgene in vitro or in vivo in cells of mammals, avian, avian, reptile, amphibian, and/or fish origin.

DETAILED DESCRIPTION OF THE PREFERRED EMBODIMENTS

The invention relates generally to plasmid DNA compositions and methods to improve the duration of plasmid-directed transgene expression. The invention can be practiced to improve the expression of vectors such as eukaryotic expression plasmids useful for gene therapy, genetic immunization and protein production in cell lines. It is to be understood that all references cited herein are incorporated by reference in their entirety.

According to one preferred embodiment, the present invention provides for methods of increasing plasmid-directed transgene expression of covalently closed supercoiled plasmid DNA, which comprises modifying the plasmid DNA to add one or more components selected from the group consisting of: an RNA Pol III Type II promoter, tRNA promoter, SEQ ID NO: 2, RNA Pol III Type II promoter B-box, RNA Pol III Type II promoter A-box; and transferring the modified plasmid DNA into a vertebrate cell or organism.

According to another preferred embodiment, said methods of plasmid modification improve plasmid-directed transgene expression duration in subsequent cell culture and or transfected tissue.

According to another preferred embodiment, the present invention provides methods of increasing transgene expression duration from non-integrating vector DNA comprising modifying the vector DNA to add one or more components selected from the group consisting of: an RNA Pol III Type II promoter, tRNA promoter, SEQ ID NO: 2, RNA Pol III Type II promoter B-box, RNA Pol III Type II promoter A-box; and transferring the modified viral vector DNA into a vertebrate cell or organism.

According to another preferred embodiment, said methods of vector DNA modification improve vector-directed transgene expression duration in subsequent cell culture and or transfected tissue.

According to another preferred embodiment, the present invention provides methods of increasing transgene expression duration from genomically integrated vector DNA comprising modifying the vector DNA to add one or more components selected from the group consisting of: an RNA Pol III Type II promoter, tRNA promoter, SEQ ID NO: 2, RNA Pol III Type II promoter B-box, RNA Pol III Type II promoter A-box; and integrating the modified vector DNA into a vertebrate cell or organism.

According to another preferred embodiment, said methods of vector modification improve integrated vector-directed transgene expression duration in subsequent cell culture and or transfected tissue.

According to another preferred embodiment, the present invention provides compositions of matter for construction of vectors.

According to another preferred embodiment, the present invention provides compositions for construction of a vector comprising one or more anti-silencing elements with at least 90% sequence identity to the sequence set forth as SEQ ID NO: 2, and a vector DNA replicon, wherein said anti-silencing element is operably linked to said vector DNA replicon. According to another preferred embodiment, said anti-silencing elements improves vector-directed transgene expression duration in subsequent cell culture and or transfected tissue.

As used herein, the term "sequence identity" refers to the degree of identity between any given query sequence, e.g., SEQ ID NO: 2, and a subject sequence. A subject sequence may, for example, have at least 90 percent, at least 95 percent, or at least 99 percent sequence identity to a given query sequence. To determine percent sequence identity, a query sequence (e.g., a nucleic acid sequence) is aligned to one or more subject sequences using any suitable sequence alignment program that is well known in the art, for instance, the computer program ClustalW (version 1.83, default parameters), which allows alignments of nucleic acid sequences to be carried out across their entire length (global alignment). Chema et al., *Nucleic Acids Res.*, 31(13):3497-500 (2003). In a preferred method, the sequence alignment program (e.g., ClustalW) calculates the best match between a query and one or more subject sequences, and aligns them so that identities, similarities, and differences can be determined Gaps of one or more nucleotides can be inserted into a query sequence, a subject sequence, or both, to maximize sequence alignments. For fast pair-wise alignments of nucleic acid sequences, suitable default parameters can be selected that are appropriate for the particular alignment program. The output is a sequence alignment that reflects the relationship between sequences. To further determine percent identity of a subject nucleic acid sequence to a query sequence, the sequences are aligned using the alignment program, the number of identical matches in the alignment is divided by the length of the query sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

According to another preferred embodiment, the present invention provides a composition for construction of a vector, comprising at least one anti-silencing element with at least 90% sequence identity to the sequence set forth as SEQ ID NO: 2, and a plasmid DNA replicon, wherein the anti-silencing element is operably linked to the plasmid DNA replicon. It has been surprisingly found that this anti-silencing site improves the duration of plasmid encoded transgene expression in transiently transfected cell lines, and in integrated cell lines. According to another preferred embodiment, the vector has at least 95% sequence identity to a sequence selected from the group consisting of: SEQ ID NO:1, SEQ ID NO:3.

Figure 1:
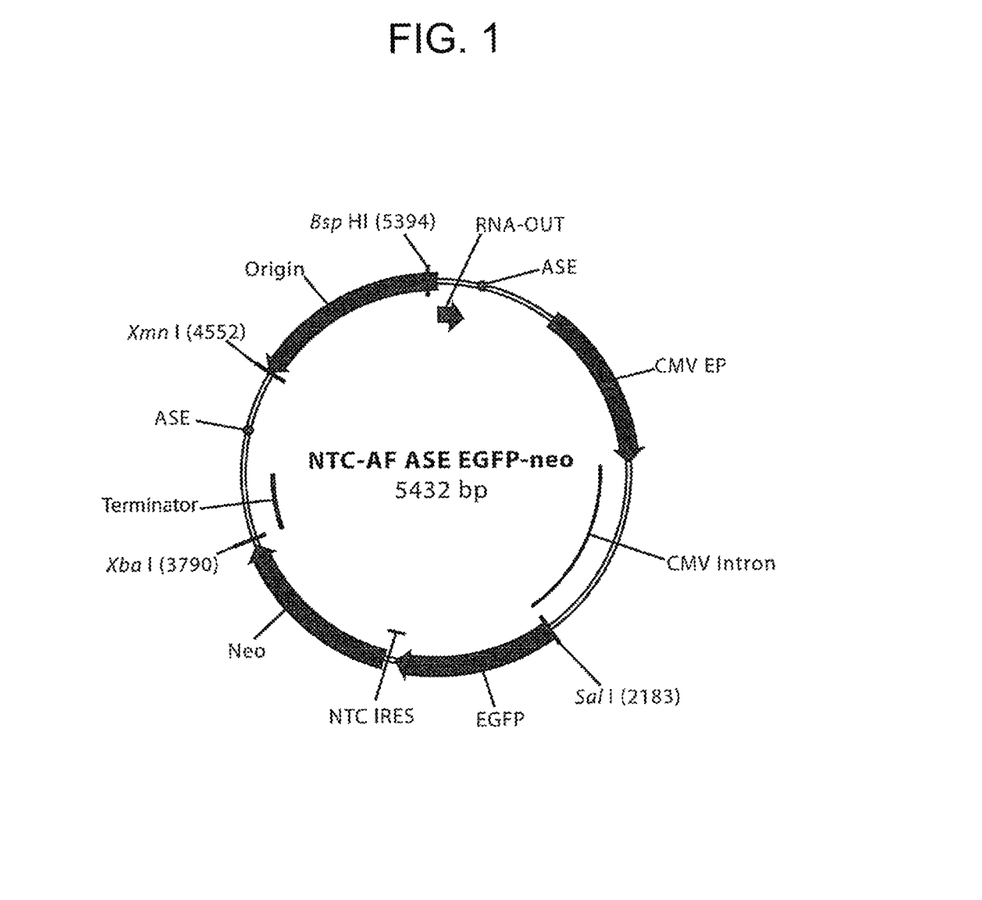
FIG. 1 NTC-AF ASE EGFP-neo.

Turning now to the drawings, FIG. 1. shows an annotated map of the NTC AF ASE EGFP-neo integration vector. Prokaryotic pUC replication origin (origin) and antibiotic-free selectable marker (RNA-OUT) are flanked by dual tRNA inserts (ASE; SEQ ID NO: 2) that shield the eukaryotic expression cassette (CMV/EP through Terminator). The neomycin resistance gene (Neo) is cloned downstream of the transgene and expressed from a novel 50 bp NTC developed IRES. After transfection of cell lines, plasmid integrants can be selected using neomycin. The vector can be linearized before transfection, at unique BspHI and/or XmnI sites in the vector backbone. SEQ ID NO:1 is the NTC AF ASE backbone (without the SalI-XbaI EGFP-neo insert).

Figure 2A:
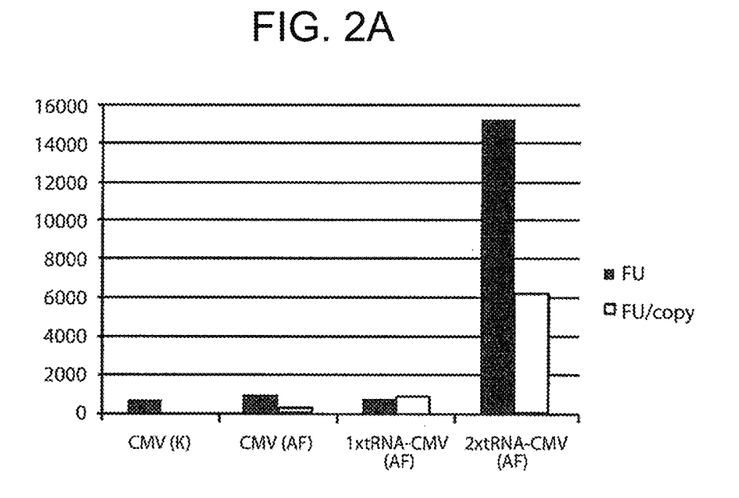
FIGS. 2A and 2B Expression after integration of NTC-AF ASE EGFP-neo versus progenitor plasmids.
Figure 2B:
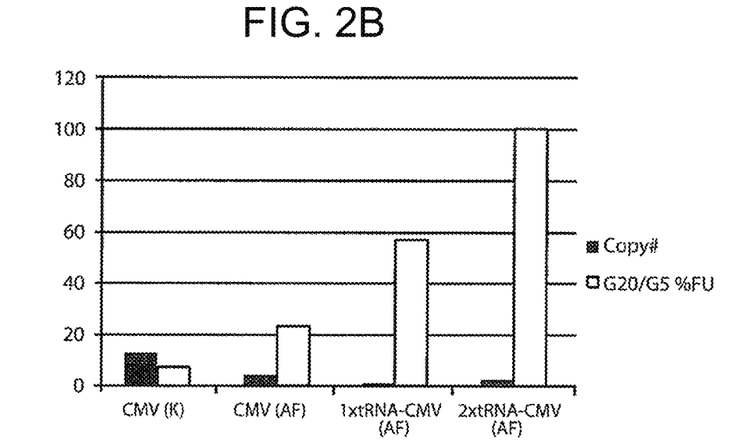

FIGS. 2A and 2B show data after integration of XmnI linearized NTC AF ASE EGFP-neo (2× tRNA-CMV (AF) and progenitor plasmids into the CHO cells line. CMV (AF) is a vector control without either ASE, 1×tRNA-CMV (AF) is a vector containing 1 ASE (the CMV promoter proximal copy). CMV (K) is a vector control without either ASE and with a kanR gene substituted for AF selection. Analysis of top integrated cell line pool from three independent transfections of EGFP transgene vector (20 generations post-integration) is shown. FU is total EGFP fluorescence; copy # is the number of integrated copies of the vector per genome equivalent (determined by qRT-PCR of isolated gDNA using an EGFP gene probe); FU/copy is total EGFP fluorescence per genome integrated copy of the vector; G20/G5% FU is the percent of the fluorescence after 5 generations post integration (G5) that is retained after 15 more generations growth (G20).

Figure 3A:
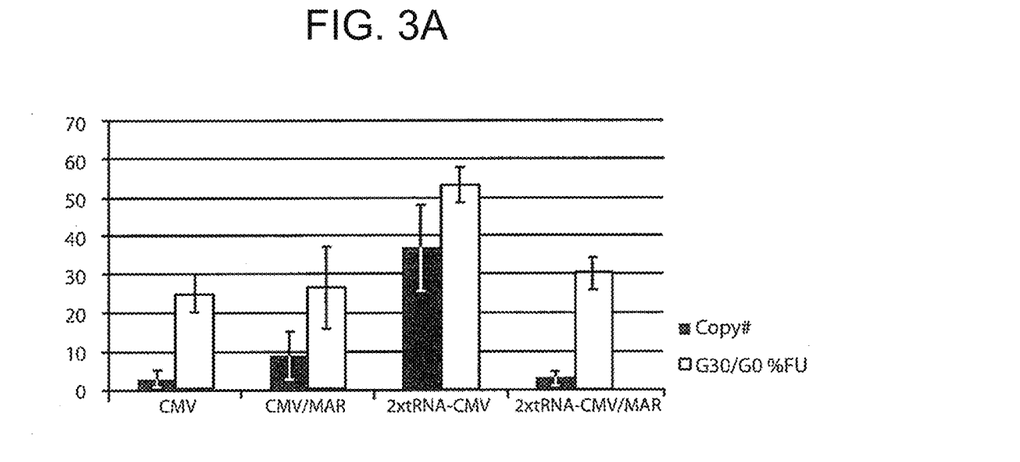
FIGS. 3A and 3B Expression after integration of NTC-AF ASE EGFP-neo versus MAR comparator.
Figure 3B:
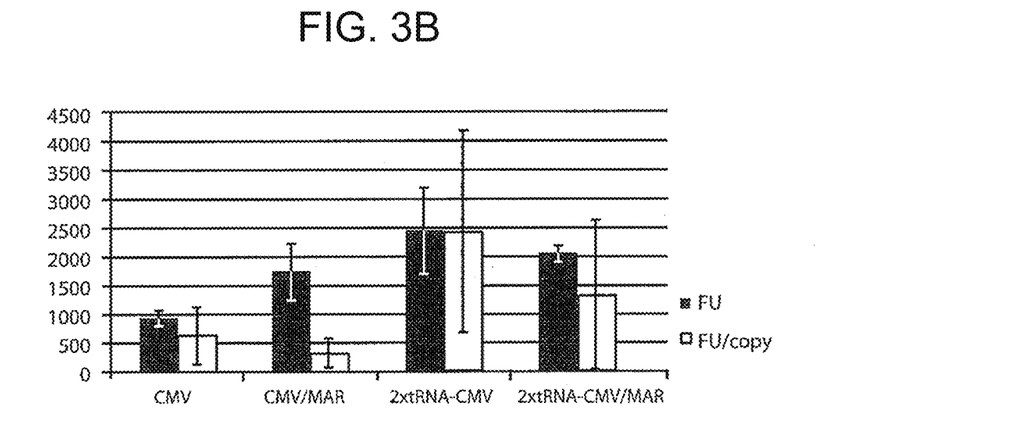

FIGS. 3A and 3B show data after integration of BspHI linearized NTC AF ASE EGFP-neo (2× tRNA-CMV) and comparator plasmids into the CHO cells line. 2×tRNA-CMV/MAR is NTC AF ASE EGFP-neo containing the chicken lysozyme MAR (Girod et al., Supra, 2005) inserted into the XmnI site. This vector was also linearized with BspHI digestion. CMV is a vector control without either ASE or a MAR and with the kanR selection gene substituted for AF RNA-OUT. CMV/MAR is this CMV vector with the chicken lysozyme MAR (Girod et al., Supra, 2005) inserted into the XmnI site. CMV and CMV/MAR vectors were linearized at a unique PvuI site in the kanR gene (due to a second BspHI site in the MAR). Average data from integrated cell line pools from three independent transfections of EGFP transgene vector (30 generations post-integration) is shown. FU is total EGFP fluorescence; copy # is the number of integrated copies of the vector per genome equivalent (determined by qRT-PCR of isolated gDNA using an EGFP gene probe); FU/copy is total EGFP fluorescence per genome integrated copy of the vector; G30/G0% FU is the percent of the fluorescence after integration (G0) that is retained after 30 generations growth (G30).

Figure 4:
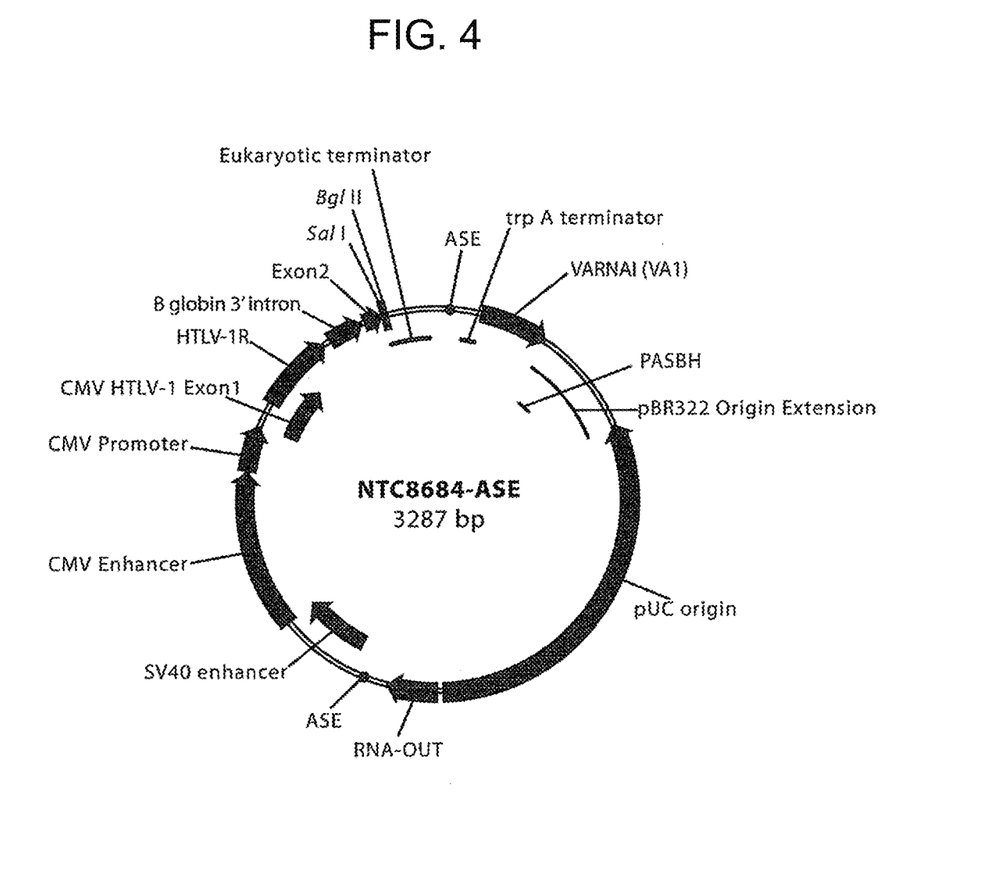
FIG. 4 NTC8685-ASE.

FIG. 4. shows an annotated map of the NTC8685-ASE vector. The pUC replication origin (origin) is extended (pBR322 Origin extension) to include a primosomal assembly site PAS-BH (this increases plasmid copy number and *E. coli* manufacturing yields). The SV40 enhancer and VA RNAI (VA1) increase transgene expression from the CMV promoter, as does the HTLV-1 R region downstream of the CMV promoter. The trpA prokaryotic terminator, VA1 gene, replication origin and RNA-OUT AF selectable marker are flanked by dual tRNA inserts (ASE; SEQ ID NO: 2) that shield the eukaryotic expression cassette (SV40 enhancer through Eukaryotic terminator). The transgene is cloned into the SalI/BglII sites, with the SalI site providing a Kozak sequence for transgene translation.

Figure 5:
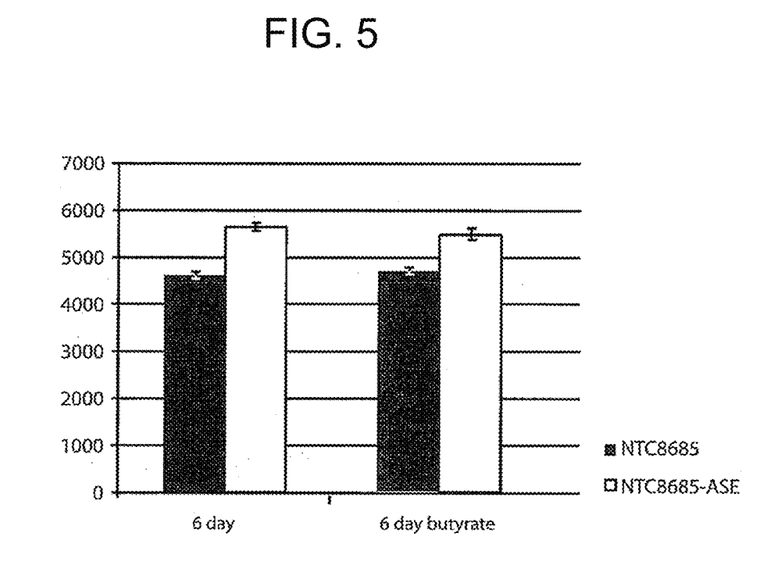
FIG. 5 Expression after transient transfection of NTC8685-ASE and NTC8685 comparator.

FIG. 5. shows expression data after transient transfection of NTC8685-ASE and NTC8685 comparator into human cell line HEK293. Fluorescence with or without sodium butyrate treatment is shown. Treatment with sodium butyrate, a histone deacetylase (HDAC) inhibitor that promotes transcription (histone acetylation destabilizes chromatin structure and facilitates transcription; Davie J R. 2003. *J. Nutr.* 133:2485S-2493S), did not affect expression from either construct demonstrating plasmid backbone catalyzed histone deacetylation-mediated gene silencing has not occurred.

Figure 6:
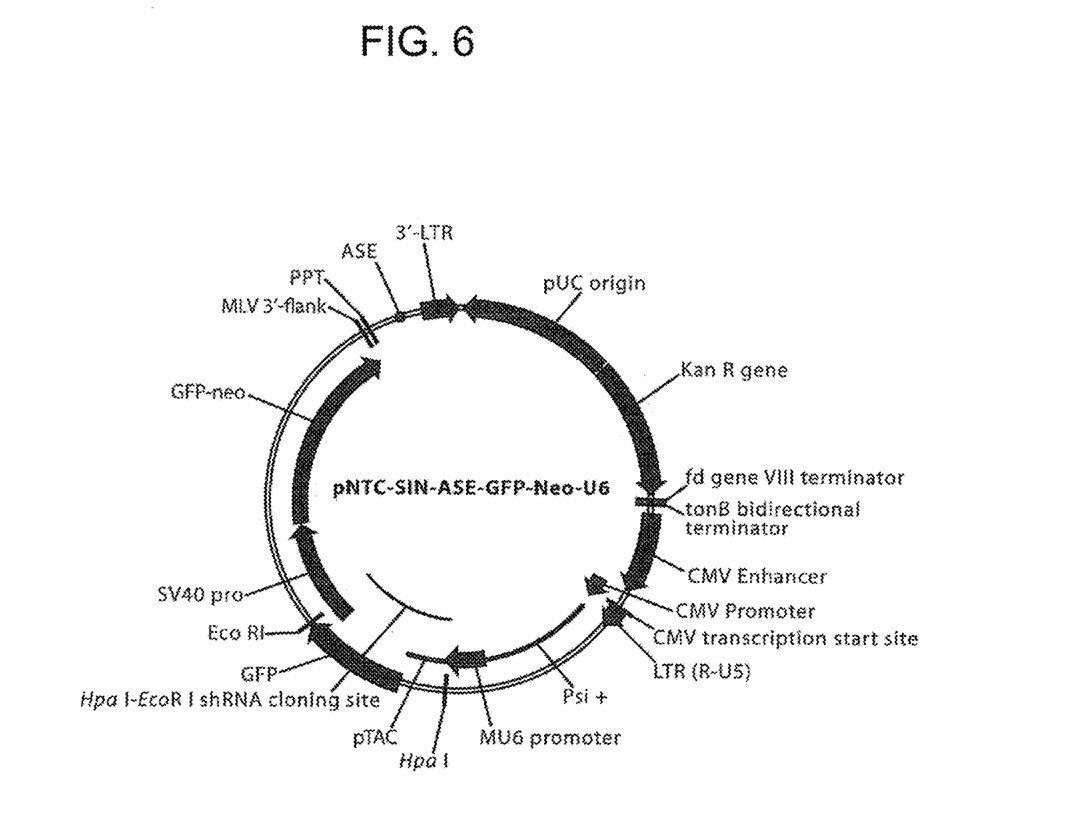
FIG. 6 pNTC-SIN-ASE-GFP-Neo-U6 retroviral vector.
Figure 7:
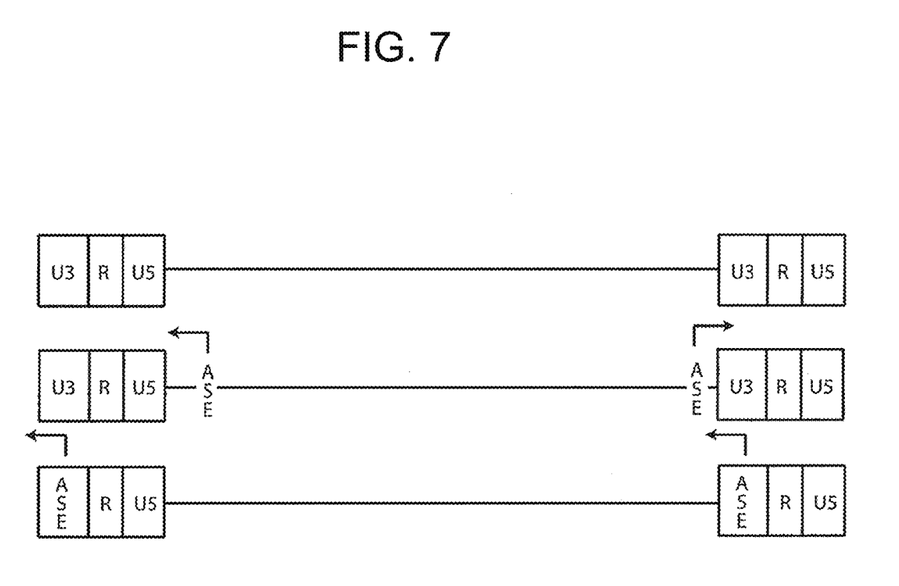
FIG. 7 Locations of ASE inserts to prevent gene silencing in retroviral vectors.
SEQ ID NO:1: NTC-AF ASE backbone
SEQ ID NO:2: Human tRNA Val ASE
SEQ ID NO:3: NTC8685-ASE

FIG. 6 shows the pNTC-SIN-ASE-GFP-Neo-U6 retroviral shRNA expression vector. The shRNA gene is clone in the HpaI-EcoRI sites, replacing the pTAC-GFP region (prokaryotic positive selection for insert). After reverse transcription and replication, the integrated vector will have both 5' and 3' UTR ASEs (in place of the U3 promoter in both LTR's) flanking the shRNA transgene, since the 3'UTR ASE is used as a replication template to insert a second ASE into the upstream LTR FIG. 7 shows the locations ASE inserts may be cloned to prevent gene silencing in retroviral vectors. Base retroviral vector (top) with either internal ASE (middle) or 3' LTR encoded ASE in place of the U3 promoter (bottom). The 3' UTR ASE is used as a replication template resulting in insertion of a second copy of the ASE into the upstream LTR prior to genome insertion.

The invention also relates to compositions and methods to improve the duration of vector-directed transgene expression. The present invention provides sequences that, when introduced into a vector backbone, increase the duration of vector-directed transgene expression.

We disclose herein the surprising observation that a RNA Polymerase III Type II promoter can be utilized to improve the duration of vector-directed transgene expression.

EXAMPLES

The methods of the invention are further illustrated by the following examples. These are provided by way of illustration and are not intended in any way to limit the scope of the invention.

Example 1

Development of AF Plasmid Vectors with Improved Duration of Vector-Directed Transgene Expression Methods: Plasmids were constructed using standard molecular biology methods (Williams, J A 2008 World Patent Application WO2008153733) and where indicated linearized by restriction enzyme digestion prior to transfection. Linearized plasmid DNA was purified by phenol/chloroform extraction and ethanol precipitation prior to resuspending in TE buffer (10 mM Tris, 1 mM EDTA, pH 8.0) for transfection. Vectors were transfected into adherent CHO or HEK293 cell lines utilizing lipofectamine LTX or lipofectamine 2000 (Invitrogen, Carlsbad, Calif.) respectively, and analyzed for duration and variability of expression in integrated and transient expression systems. Cell lines were grown in DMEM/F12 containing 10% fetal bovine serum and split (0.25% Trypsin-EDTA) using Invitrogen (Carlsbad, Calif.) reagents and conventional methodologies as described (Girod et al., Supra, 2005). Transfected cells containing genomically integrated plasmid were selected using 500 µg/mL geneticin (Invitrogen, Carlsbad, Calif.) in media over 10 days. Transgene expression (EGFP fluorescence) was quantified using a BioTek FLx800 microplate fluorescence reader (total expression) and by fluorescence microscopy (expression variability). Genomic DNA was isolated from integrated cell lines using the DNeasy blood and tissue kit (Qiagen Sciences, MD) and total DNA quantified using the BioTek FLx800 microplate fluorescence reader by determining picogreen (Invitrogen, Carlsbad, Calif.) fluorescence of samples versus a linearized vector standard curve. qRT-PCR to quantify vector copies in gDNA used a TaqMan EGFP transgene MGB probe and flanking primers in a TaqMan Gene expression assay using Applied Biosystems (Foster City Calif.) TaqMan reagents and MGB probe and a Step One Real Time PCR System (Applied Biosystems, Foster City Calif.). Linearized vector was used for the qRT-PCR standard curve.

Results: An antibiotic-free (AF) vertebrate expression vector was modified for maximal and prolonged expression after genome integration. Insertion of a tRNA Val promoter (SEQ ID NO: 2) upstream of the CMV enhancer (FIG. 1) surprisingly resulted in improved transgene expression in transient transfection (data not shown), and after genome integration (Table 1). This improved expression was comparable to that obtained using the chicken lysozyme Matrix Attachment Site MAR, without the dramatic increase in genome integration observed with the MAR. This is reflected by the superior FU/integrated copy obtained with the tRNA Val construct (Table 1).

TABLE 1

Analysis of single tRNA Val insertion upstream of the CMV promoter

| Vector[d] | G23 FU[a,c] | G23 FU/ copy (pool) | G23 Copy#/ genome | G23 % total[b] | G23 Mean FU[b] |
|---|---|---|---|---|---|
| CMV (AF) | 302 ± 176 | 82 | 3.7 | 27.7 | 1077 |
| 1xtRNA CMV (AF) | 462 ± 341 | 462 | 1 | 33.4 | 1282 |
| CMV | 243 ± 157 | 187 | 1 | 24.5 | 885 |
| CMV-MAR | 874 ± 691 | 56 | 15.7 | 54.4 | 1309 |

[a]G19/G0 % FU was 39 ± 26 (AF-CMV), 40 ± 19 (AF-tRNAVAL-CMV), 33 ± 19 (CMV) and 52 ± 26 (CMV-MAR).
[b]Fluorescence Activated cell sorting (FACS) using the BD FACSCalibur (BD Biosciences, San Jose, CA). Percent cells with fluorescence signal about background (% total) and mean fluorescence value (Mean FU). Cells were gated such that a negative control (CHO cells without EGFP) gave 0.5 (% total) and 27 (Mean FU).
[c]Supercoiled plasmid was transfected (six replicates) into CHO cells and integrants selected. Results are mean ± SD for the six replicates.
[d]Vectors were integrated and analyzed at G0, G19 and G20 (generations growth). CMV (AF) is a vector control without either ASE, 1xtRNA-CMV (AF) is a vector containing 1 ASE (the CMV promoter proximal copy of tRNA Val; FIG. 1). CMV is a vector control without either ASE or a MAR and with the kanR selection gene substituted for AF RNA-OUT. CMV/MAR is this CMV vector with the chicken lysozyme MAR (Girod et al., Supra, 2005) inserted into the XmnI site.

Insertion of a second tRNA Val promoter (SEQ ID NO:2) after the eukaryotic terminator (i.e., flanking the eukaryotic expression cassette; FIG. 1) surprisingly resulted in further improved transgene expression after genome integration. Integrated copies also had reduced transgene silencing (FIGS. 2A-2B and 3A-3B).

An antibiotic-free vertebrate expression vector incorporating tRNA genes was then developed (NTC8685-ASE; SEQ ID NO:3) for maximal and prolonged expression after transient transfection (FIG. 4). Insertion of the SEQ ID NO: 2 tRNA promoter upstream and downstream of the eukaryotic expression cassette (FIG. 4) surprisingly resulted in improved transgene expression after extended cell culture growth (6 days post transfected) in HEK293 (and CHO cells) after transient transfection of an EGFP transgene expressing version (FIG. 5).

Discussion: The AF ASE vectors disclosed herein have a minimal prokaryotic backbone with antibiotic free selectable marker (Luke, J., Carnes, A. E., Hodgson, C. P., and Williams, J. A. (2009). Vaccine 27: 6454-6459) and further incorporate tRNA genes flanking the expression cassette to prevent gene silencing. These ASE vectors outperform a chicken lysozyme Matrix Attachment Site (MAR) comparator vector for expression level and prolonged expression without increasing genome insertion rate as MAR's do (FIGS. 3A and 3B), and are thus smaller, more potent, safer alternatives to improve gene transfer.

Thus, the reader will see that the improved vectors of the invention provide for a rational approach to improve the duration of vector-encoded transgene expression from either non-integrating (transiently transfected) or integration vectors. This invention solves the long unsolved need of a small element that prevents transgene silencing in vertebrate expression vectors; current methods to improve the duration of transgene expression either 1) require large DNA inserts (e.g. 3 kb chicken lysozyme MAR) that reduce vector potency and/or limit the size left for a transgene, or 2) have inefficient manufacturing (e.g. minicircle vectors) that increase production cost. Each ASE is only 70-80 bp, and can be easily incorporated into an existing vector-manufacturing platform.

While the basis for expression improvement is unknown, optimal vectors are expected to have a longer duration in transgene expression due to a decrease in gene silencing mediated by a reduction of expression inhibiting factors and/or incorporation of expression promoting factors. While some RNA polymerase II and III promoters and TFIIIC binding sites have been described as heterochromatin barriers and or chromatin insulators in yeast (Donze D, Kamakaka R T. 2001. EMBO J. 20: 520-531; Simms T A, Dugas S L, Gremillion J C, Ibos M E, Dandurand N, Toliver T T, Edwards D J, Donze D. 2008. Eukaryotic Cell 7: 2078-2086) other tRNA genes promote transcriptional silencing in lower eukaryotes (Inner H, Henning I, Bruchhaus I, Tannich E. 2010. Eukaryotic Cell 9: 306-314; Wang L, Haeusler R A, Good P D, Thompson M, Nagar S, Engelke D R. 2005. Journal Biological Chemistry 280: 8637-8639). Boundary site function of RNA Polymerase III promoters has not been described in higher eukaryotes such as vertebrates. A domain boundary in a murine SINE B2 repeat has been demonstrated to require both divergent RNA Pol II and Pol III promoters for function (Lunyak V V, Prefontaine G G, Nunez E, Cramer T, Ju B G, Ohgi K A, Hutt K, Roy R, Garcia-Diaz A, Zhu X, Yung Y, Montoliu L, Glass C K, Rosenfeld M G. 2007. Science 317: 248-251). This teaches away from the current invention in which the presence of a RNA Pol III promoter prevents gene silencing.

While not limiting the application of the invention, inclusion of a type II RNA Pol III promoter such as tRNA Val may be beneficial in preventing gene silencing through recruitment of a transcription factor (e.g. TFIIIC to the A and B boxes), or through active RNA Pol III transcription, that create boundaries that limit deacetylated histone containing inhibitor chromatin spread from flanking sequences (plasmid or genomic). Alternatively, CpG islands near the transcription start site may be protected from inactivation due to CpG methylation.

While the above description contains many examples, these should not be construed as limitations on the scope of the invention, but rather should be viewed as an exemplification of preferred embodiments thereof. Many other variations are possible. For example, the vector AF selectable marker may be substituted with an alternative selectable marker. Likewise, the vectors may contain alternative promoters, terminators and/or transgenes to the examples provided herein. The orientation of the various vector-encoded elements may be changed relative to each other. The vectors may optionally contain additional functionalities, such as nuclear localizing sequences, the adenoviral VA RNAI, and/or immunostimulatory RNA elements as disclosed in Williams, Supra 2008. Vectors containing combinations of anti-silencing elements could be rapidly created and screened for improved duration of expression. The ASE sequences could also be cloned into a variety of non-integrating viral vectors to effect improved transgene expression.

The ASE sequences could also be cloned into a variety of integrating viral (e.g. retroviral, lentiviral) or non-viral (e.g. within the terminal repeats of transposon vectors such as sleeping beauty or integration sites of phage phiC31 integrase vectors). An example application of the ASE sequences to improve the duration of expression from a retroviral vector is shown in FIGS. 6 and 7). An investigator of average skill in the art of vector design could apply the approaches described herein to modify other viral or non-viral vectors with ASE sequences to improve the duration of transgene expression.

Accordingly, the scope of the invention should be determined not by the embodiments illustrated, but by the appended claims.

What is claimed is:

1. A method of improving the duration of transgene expression, the method comprising: a) providing an expression vector comprising a prokaryotic replication origin, a selectable marker, a eukaryotic expression cassette and tRNA promoters upstream and downstream of the eukaryotic expression cassette, said tRNA promoters each comprising the two intragenic promoter elements RNA pol III type II promoter A-box and B-box, said tRNA promoters preventing gene silencing, said eukaryotic expression cassette comprising the transgene under the control of a heterologous promoter; and b) introducing said expression vector into a target vertebrate cell or a vertebrate organism comprising the target vertebrate cells, under conditions wherein the target vertebrate cells are transfected and said transgene is expressed, wherein the duration of transgene expression is greater than achieved with the same vector lacking said tRNA promoters upstream and downstream of the eukaryotic expression cassette.

2. The method of claim 1, wherein said tRNA promoters comprise the human tRNA valine promoter nucleic acid sequence of SEQ ID NO:2.

3. The method of claim 1, wherein said vector is selected from the group consisting of: a non-viral vector, a viral vector, an integrating vector, a non-integrating vector, and a plasmid.

4. A method of improving the duration of transgene expression, the method comprising: a) providing an expression vector comprising a prokaryotic replication origin, an antibiotic-free selectable marker, a eukaryotic expression cassette and tRNA promoters upstream and downstream of the eukaryotic expression cassette, said tRNA promoters each comprising the two intragenic promoter elements RNA pol III type II promoter A-box and B-box, said tRNA promoters preventing, gene silencing, said eukaryotic expression cassette comprising the transgene under the control of a heterologous promoter; and b) linearizing, said vector in the vector backbone; and
c) introducing said expression vector into a target vertebrate cell or a vertebrate organism comprising the target vertebrate cells, under conditions wherein the target vertebrate cells are transfected and said transgene is expressed, wherein the duration of transgene expression is greater than achieved with the same vector lacking said tRNA promoters upstream and downstream of the eukaryotic expression cassette.

5. The method of claim 4, wherein said vector is selected from the group consisting of: a non-viral vector, a viral vector, an integrating vector, a non-integrating vector, and a plasmid.

6. The method of claim 4, wherein said tRNA promoters comprise the human tRNA valine promoter nucleic acid sequence of SEQ ID NO:2.

7. A method of improving the duration of transgene expression, the method comprising: a) providing an expression vector comprising a prokaryotic replication origin, an antibiotic-free selectable marker, a eukaryotic expression, cassette and tRNA promoters upstream and downstream of the eukaryotic expression cassette, wherein said tRNA promoters comprise the human tRNA valine promoter nucleic acid sequence of SEQ NO:2, said tRNA promoters preventing gene silencing, said eukaryotic expression cassette comprising i) the transgene under the control of a heterologous promoter; and b) introducing said expression vector into a target vertebrate cell or a vertebrate organism comprising the target vertebrate cells, under conditions wherein the target vertebrate cells are transfected and said transgene is expressed, wherein the duration of transgene expression is greater than achieved with the same vector lacking, said tRNA promoters upstream and downstream of the eukaryotic expression cassette.

* * * * *

SEQUENCE LISTING

```
<160> NUMBER OF SEQ ID NOS: 3

<210> SEQ ID NO 1
<211> LENGTH: 3831
<212> TYPE: DNA
<213> ORGANISM: Artificial Sequence
<220> FEATURE:
<223> OTHER INFORMATION: Description of Artificial Sequence: NTC-AF ASE
      backbone

<400> SEQUENCE: 1
gtggtagaat tggtaaagag agtcgtgtaa aatatcgagt tcgcacatct tgttgtctga      60
ttattgattt ttggcgaaac catttgatca tatgacaaga tgtgtatcta ccttaactta     120
atgattttga taaaaatcat taggtacccc ggctctagcg ttgttggttt gtagtgcccg     180
gtttcgaacc ggggaccttt cgcgtgttag gcgaacgtga taaccactac actacggaaa     240
ccaacggtgc tagctagatg gcatgacatt aacctataaa aataggcgta tcacgaggcc     300 cttttcgtctc gcgcgtttcg gtgatgacgg tgaaaacctc tgacacatgc agctcccgga    360
gacggtcaca gcttgtctgt aagcggatgc cgggagcaga caagcccgtc agggcgcgtc     420
agcgggtgtt ggcgggtgtc ggggctggct taactatgcg gcatcagagc agattgtact     480
gagagtgcac catatgcggt gtgaaatacc gcacagatgc gtaaggagaa ataccgcat      540 cagattggct attggccatt gcatacgttg tatccatatc ataatatgta catttatatt     600
ggctcatgtc caacattacc gccatgttga cattgattat tgactagtta ttaatagtaa     660
tcaattacgg ggtcattagt tcatagccca tatatggagt tccgcgttac ataacttacg     720
gtaaatggcc cgcctggctg accgcccaac gacccccgcc cattgacgtc aataatgacg     780
tatgttccca tagtaacgcc aatagggact ttccattgac gtcaatgggt ggagtattta     840
cggtaaactg cccacttggc agtacatcaa gtgtatcata tgccaagtac gccccctatt     900
gacgtcaatg acggtaaatg gcccgcctgg cattatgccc agtacatgac cttatgggac     960
tttcctactt ggcagtacat ctacgtatta gtcatcgcta ttaccatggt gatgcggttt    1020
tggcagtaca tcaatgggcg tggatagcgg tttgactcac ggggatttcc aagtctccac    1080
cccattgacg tcaatgggag tttgttttgg caccaaaatc aacgggactt tccaaaatgt    1140
cgtaacaact ccgccccatt gacgcaaatg ggcggtaggc gtgtacggtg ggaggtctat    1200
ataagcagag ctcgtttagt gaaccgtcag atcgcctgga gacgccatcc acgctgtttt    1260
gacctccata gaagacaccg ggaccgatcc agcctccgcg gccgggaacg gtgcattgga    1320
acgcggattc cccgtgccaa gagtgacgta agtaccgcct atagactcta taggcacacc    1380
cctttggctc ttatgcatgc tatactgttt ttggcttggg gcctatacac ccccgcttcc    1440
ttatgctata ggtgatggta tagcttagcc tataggtgtg ggttattgac cattattgac    1500
cactccccta ttggtgacga tactttccat tactaatcca taacatggct ctttgccaca    1560
actatctcta ttggctatat gccaatactc tgtccttcag agactgacac ggactctgta    1620
```

-continued

```
tttttacagg atggggtccc atttattatt tacaaattca catatacaac aacgccgtcc    1680
cccgtgcccg cagtttttat taaacatagc gtgggatctc cacgcgaatc tcgggtacgt    1740
gttccggaca tgggctcttc tccggtagcg gcggagcttc cacatccgag ccctggtccc    1800
atgcctccag cggctcatgg tcgctcggca gctccttgct cctaacagtg gaggccagac    1860
ttaggcacag cacaatgccc accaccacca gtgtgccgca caaggccgtg cggtagggt     1920
atgtgtctga aaatgagcgt ggagattggg ctcgcacggc tgacgcagat ggaagactta    1980
aggcagcggc agaagaagat gcaggcagct gagttgttgt attctgataa gagtcagagg    2040
taactcccgt tgcggtgctg ttaacggtgg agggcagtgt agtctgagca gtactcgttg    2100
ctgccgcgcg cgccaccaga cataatagct gacagactaa cagactgttc ctttccatgg    2160
gtcttttctg cagtcaccgt cgtcgactct agagatctgt gtgttggttt tttgtggatc    2220
tgctgtgcct tctagttgcc agccatctgt tgtttgcccc tcccccgtgc cttccttgac    2280
cctggaaggt gccactccca ctgtcctttc ctaataaaat gaggaaattg catcgcattg    2340
tctgagtagg tgtcattcta ttctgggggg tggggtgggg cagcacagca aggggaggga    2400
ttgggaagac aatagcaggc atgctgggga tgcggtgggc tctatgggta cctctctctc    2460
tctctctctc tctctctctc tctctctctc tcggtacctc tctctctctc tctctctctc    2520
tctctctctc tctctctcgg taccaggtgc tgaagaattg acccggttcc tcctgggcca    2580
gaaagaagca ggcacatccc cttctctgtg acacaccctg tccacctagc accgttggtt    2640
tccgtagtgt agtggttatc acgttcgcct aacacgcgaa aggtccccgg ttcgaaaccg    2700
ggcactacaa accaacaacg ctggttctta gttccagccc cactcatagg acactcatag    2760
ctcaggaggg ctccgccttc aatcccaccc gctaaagtac ttggagcggt ctctccctcc    2820
ctcatcagcc caccaaaacca aacctagcct ccaagagtgg gaagaaatta agcaagata    2880
ggctattaag tgcagaggga gagaaaatgc ctccaacatg tgaggaagta atgagagaaa    2940
tcatagaatt tcttccgctt cctcgctcac tgactcgctg cgctcggtcg ttcggctgcg    3000
gcgagcggta tcagctcact caaaggcggt aatacggtta ccacagaat cagggataa     3060
cgcaggaaag aacatgtgag caaaaggcca gcaaaaggcc aggaaccgta aaaaggccgc    3120
gttgctggcg ttttttccata ggctccgccc ccctgacgag catcacaaaa atcgacgctc    3180
aagtcagagg tggcgaaacc cgacaggact ataaagatac caggcgtttc ccctggaag   3240
ctccctcgtg cgctctcctg ttccgaccct gccgcttacc ggatacctgt ccgcctttct    3300
cccttcggga agcgtggcgc tttctcaatg ctcacgctgt aggtatctca gttcggtgta    3360
ggtcgttcgc tccaagctgg gctgtgtgca cgaaccccc gttcagcccg accgctgcgc    3420
cttatccggt aactatcgtc ttgagtccaa cccggtaaga cacgacttat cgccactggc    3480
agcagccact ggtaacagga ttagcagagc gaggtatgta ggcggtgcta cagagttctt    3540
gaagtggtgg cctaactacg gctacactag aaggacagta tttggtatct gcgctctgct    3600
gaagccagtt accttcggaa aaagagttgg tagctcttga tccggcaaac aaaccaccgc    3660
tggtagcggt ggttttttttg tttgcaagca gcagattacg cgcagaaaaa aaggatctca    3720
agaagatcct ttgatctttt ctacgggggtc tgacgctcag tggaacgaaa actcacgtta    3780
agggattttg gtcatgagat tatcaaaaag gatcttcacc tagatccttt t            3831
```

<210> SEQ ID NO 2
<211> LENGTH: 73
<212> TYPE: DNA
<213> ORGANISM: Artificial Sequence

```
<220> FEATURE:
<223> OTHER INFORMATION: Description of Artificial Sequence: human tRNA
      val ASE

<400> SEQUENCE: 2
accgttggtt tccgtagtgt agtggttatc acgttcgcct aacacgcgaa aggtccccgg    60
ttcgaaaccg ggc                                                       73

<210> SEQ ID NO 3
<211> LENGTH: 3287
<212> TYPE: DNA
<213> ORGANISM: Artificial Sequence
<220> FEATURE:
<223> OTHER INFORMATION: Description of Artificial Sequence: NTC8685-ASE

<400> SEQUENCE: 3
accgttggtt tccgtagtgt agtggttatc acgttcgcct aacacgcgaa aggtccccgg    60
ttcgaaaccg ggcactacaa accaacccgc ctaatgagcg ggcttttttt tcttagggtg   120
caaaaggaga gcctgtaagc gggcactctt ccgtggtctg gtggataaat tcgcaagggt   180
atcatggcgg acgaccgggg ttcgagcccc gtatccggcc gtccgccgtg atccatgcgg   240
ttaccgcccg cgtgtcgaac ccaggtgtgc gacgtcagac aacgggggag tgctcctttt   300
ggcttccttc ccctaccggt ctgcctcgcg cgtttcggtg atgacggtga aaacctctga   360
cacatgcagc tcccggagac ggtcacagct tgtctgtaag cggatgccgg gagcagacaa   420
gcccgtcagg gcgcgtcagc gggtgttggc gggtgtcggg gcgcagccat gacccagtca   480
cgtagcgata gcggagtgta tactggctta actatgcggc atcagagcag attgtactga   540
gagtgcacca tatgcggtgt gaaataccgc acagatgcgt aaggagaaaa taccgcatca   600
ggcgctcttc cgcttcctcg ctcactgact cgctgcgctc ggtcgttcgg ctgcggcgag   660
cggtatcagc tcactcaaag gcggtaatac ggttatccac agaatcaggg gataacgcag   720
gaaagaacat gtgagcaaaa ggccagcaaa aggccaggaa ccgtaaaaag gccgcgttgc   780
tggcgttttt ccataggctc cgcccccctg acgagcatca caaaaatcga cgctcaagtc   840
agaggtggcg aaacccgaca ggactataaa gataccaggc gtttccccct ggaagctccc   900
tcgtgcgctc tcctgttccg accctgccgc ttaccggata cctgtccgcc tttctccctt   960
cgggaagcgt ggcgctttct catagctcac gctgtaggta tctcagttcg gtgtaggtcg  1020
ttcgctccaa gctgggctgt gtgcacgaac cccccgttca gcccgaccgc tgcgccttat  1080
ccggtaacta tcgtcttgag tccaacccgg taagacacga cttatcgcca ctggcagcag  1140
ccactggtaa caggattagc agagcgaggt atgtaggcgg tgctacagag ttcttgaagt  1200
ggtggcctaa ctacggctac actagaagaa cagtatttgg tatctgcgct ctgctgaagc  1260
cagttacctt cggaaaaaga gttggtagct cttgatccgg caaacaaacc accgctggta  1320
gcggtggttt ttttgtttgc aagcagcaga ttacgcgcag aaaaaaagga tctcaagaag  1380
atcctttgat cttttctacg ggtctgacgc tcagtggaac gaaaactca cgttaaggga  1440 ttttggtcat gagattatca aaaaggatct tcacctagat ccttttaaat taaaaatgaa  1500
gttttaaatc aatctaaagt atatatgagt aaacttggtc tgacagttac caatgcttaa  1560
tcagtgaggc acctatctca gcgatctgtc tatttcgttc atccatagtt gcctgactcc  1620
tgcaaaccac gttgtggtag aattggtaaa gagagtcgtg taaatatcg agttcgcaca  1680 tcttgttgtc tgattattga tttttggcga accatttga tcatatgaca agatgtgtat  1740
ctaccttaac ttaatgattt tgataaaaat cattaggtac cccggctcta gcgttgttgg  1800
```

-continued

```
tttgtagtgc ccggtttcga accggggacc tttcgcgtgt taggcgaacg tgataaccac    1860
tacactacgg aaaccaacgg tgctagccct gatcactgtg gaatgtgtgt cagttagggt    1920
gtggaaagtc cccaggctcc ccagcaggca gaagtatgca aagcatgcat ctcaattagt    1980
cagcaaccag gtgtggaaag tccccaggct ccccagcagg cagaagtatg caaagcatgc    2040
atctcaatta gtcagcaacc atagtcccgc ccctaactcc gcccatcccg cccctaactc    2100
cgcccagtta cggggtcatt agttcatagc ccatatatgg agttccgcgt tacataactt    2160
acggtaaatg gcccgcctgg ctgaccgccc aacgaccccc gcccattgac gtcaataatg    2220
acgtatgttc ccatagtaac gccaataggg actttccatt gacgtcaatg ggtggagtat    2280
ttacggtaaa ctgcccactt ggcagtacat caagtgtatc atatgccaag tacgccccct    2340
attgacgtca atgacggtaa atggcccgcc tggcattatg cccagtacat gaccttatgg    2400
gactttccta cttggcagta catctacgta ttagtcatcg ctattaccat ggtgatgcgg    2460
ttttggcagt acatcaatgg gcgtggatag cggtttgact cacggggatt tccaagtctc    2520
caccccattg acgtcaatgg gagtttgttt tggcaccaaa atcaacggga ctttccaaaa    2580
tgtcgtaaca actccgcccc attgacgcaa atgggcggta ggcgtgtacg gtgggaggtc    2640
tatataagca gagctcgttt agtgaaccgt cagatcgcct ggagacgcca tccacgctgt    2700
tttgacctcc atagaagaca ccgggaccga tccagcctcc gcggctcgca tctctccttc    2760
acgcgcccgc cgccctacct gaggccgcca tccacgccgg ttgagtcgcg ttctgccgcc    2820
tcccgcctgt ggtgcctcct gaactgcgtc cgccgtctag gtaagtttaa agctcaggtc    2880
gagaccgggc ctttgtccgg cgctcccttg gagcctacct agactcagcc ggctctccac    2940
gctttgcctg accctgcttg ctcaactcta gttctctcgt taacttaatg agacagatag    3000
aaactggtct tgtagaaaca gagtagtcgc ctgcttttct gccaggtgct gacttctctc    3060
ccctgggctt ttttcttttt ctcaggttga aagaagaag acgaagaaga cgaagaagac    3120
aaaccgtcgt cgacagatct ttttccctct gccaaaaatt atggggacat catgaagccc    3180
cttgagcatc tgacttctgg ctaataaagg aaatttattt tcattgcaat agtgtgttgg    3240
aattttttgt gtctctcact cggaaggaca taagggcggc cgctagc                  3287
```